(12) United States Patent
Hermle et al.

(10) Patent No.: US 8,317,203 B2
(45) Date of Patent: Nov. 27, 2012

(54) COUPLING DEVICE FOR ATTACHING MEDICAL INSTRUMENTS TO A HOLDING DEVICE

(75) Inventors: Rainer Hermle, Gosheim (DE); Andreas Efinger, Rietheim (DE)

(73) Assignee: Karl Storz GmbH & Co. KG (DE)

( * ) Notice: Subject to any disclaimer, the term of this patent is extended or adjusted under 35 U.S.C. 154(b) by 1189 days.

(21) Appl. No.: 12/147,170

(22) Filed: Jun. 26, 2008

(65) Prior Publication Data
US 2009/0001676 A1 Jan. 1, 2009

(30) Foreign Application Priority Data
Jun. 29, 2007 (DE) .......................... 10 2007 030 310

(51) Int. Cl.
*B23B 31/20* (2006.01)
(52) U.S. Cl. .................. 279/23.1; 279/43.2; 279/46.3; 279/140; 279/906
(58) Field of Classification Search .................. 279/23.1, 279/42, 43.2, 43.4, 46.3, 48, 140, 906; *B23B 31/20*
See application file for complete search history.

(56) References Cited

U.S. PATENT DOCUMENTS

| | | | |
|---|---|---|---|
| 1,190,491 A | 7/1916 | Watts et al. | |
| 3,756,634 A | 9/1973 | McGlothlin | |
| 3,782,838 A | 1/1974 | Tiraspolsky et al. | |
| 5,167,476 A * | 12/1992 | Lafferty et al. | 408/240 |
| 5,674,225 A | 10/1997 | Müller | |
| 8,029,216 B2 * | 10/2011 | Guy | 408/240 |
| 2007/0270640 A1 | 11/2007 | Dimitriou et al. | |

FOREIGN PATENT DOCUMENTS

| | | |
|---|---|---|
| DE | 9108078 U1 | 8/1991 |
| DE | 20317693 U1 | 3/2005 |
| DE | 10357104 A1 | 7/2005 |
| EP | 0418620 A2 | 3/1991 |

OTHER PUBLICATIONS

German Search Report, dated Jan. 9, 2008, 4 pages.
European Search Report; EP 08 00 9665; Nov. 12, 2008; 6 pages.

* cited by examiner

*Primary Examiner* — Eric A Gates
(74) *Attorney, Agent, or Firm* — St. Onge Steward Johnston & Reens LLC

(57) ABSTRACT

A coupling device for securing medical instruments to a holding device allows for simple and rapid handling and exact positioning of the medical instrument. A coupler socket is configured on one component and a coupler plug is configured on the other component, wherein the coupler socket and coupler plug can be fixed in mutually connected position with respect to one another by means of at least one locking element. The coupler socket is configured as a sleeve-shaped collet chuck including several mutually distanced spring arms. The coupler plug includes a coupling pin equipped with at least one radially outward-pointing catch cam. When coupled, at least one catch cam of the coupling pin catches on a corresponding back-cut on the collet chuck. The locking element can be screwed onto the collet chuck so that the spring arms of the collet chuck in the coupled position are affixed facing radially outward.

8 Claims, 3 Drawing Sheets

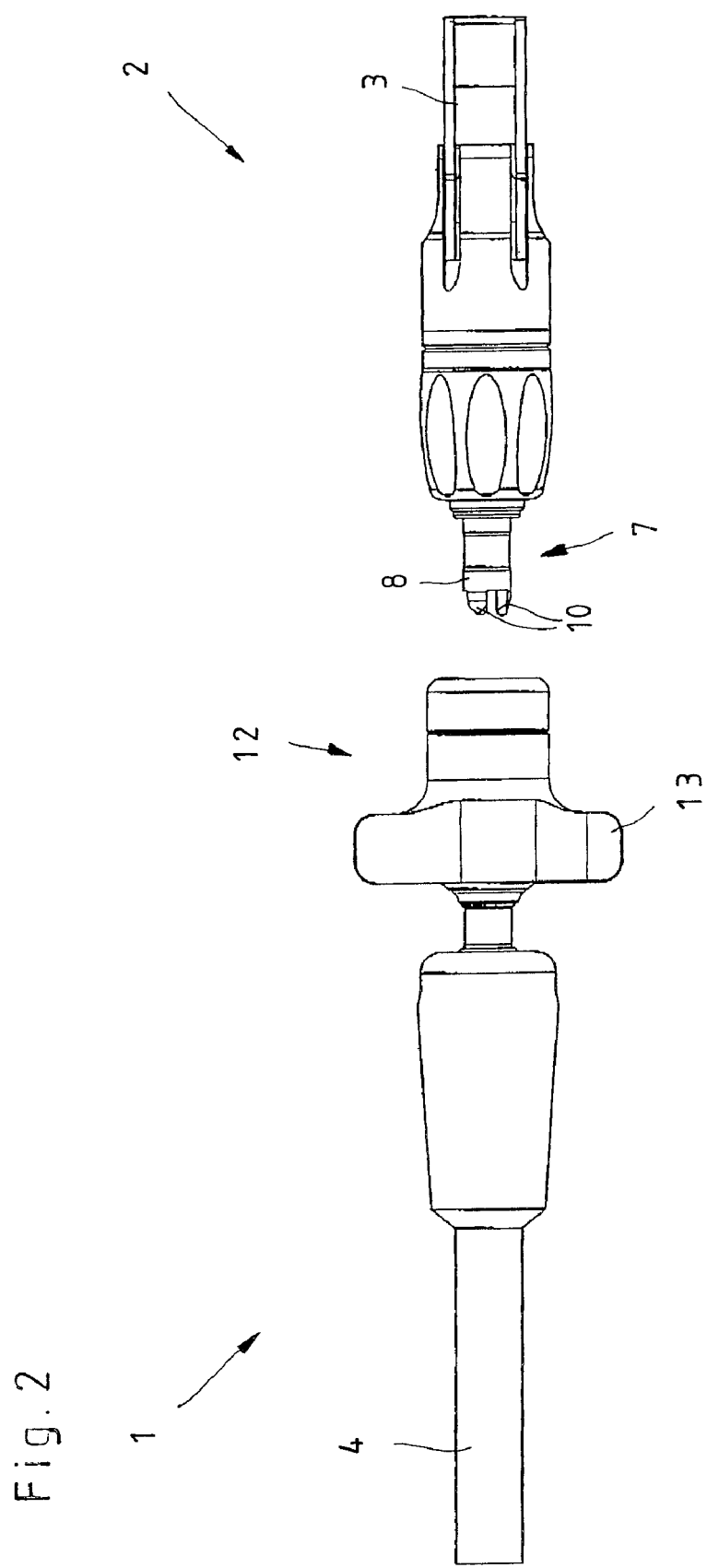

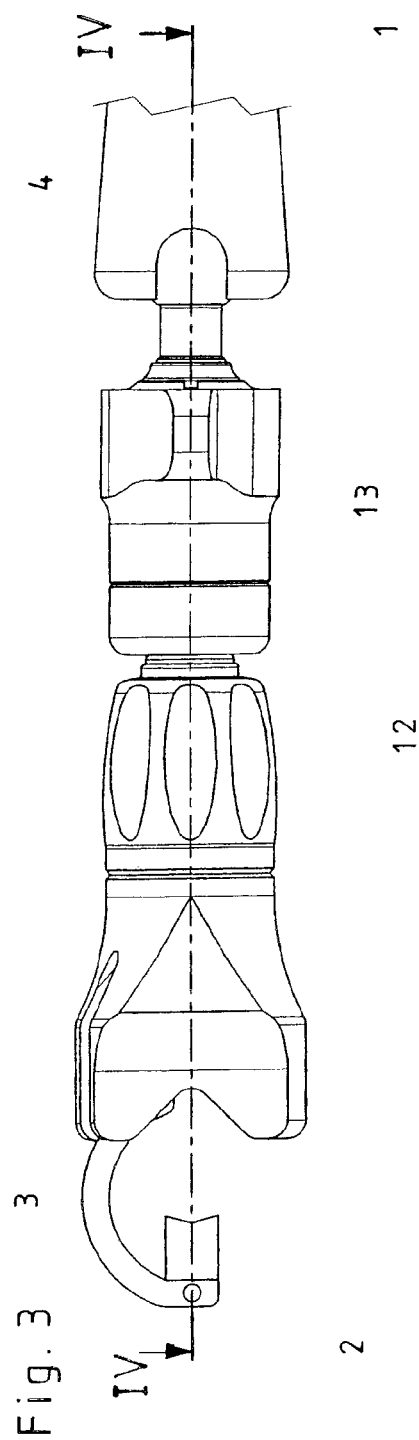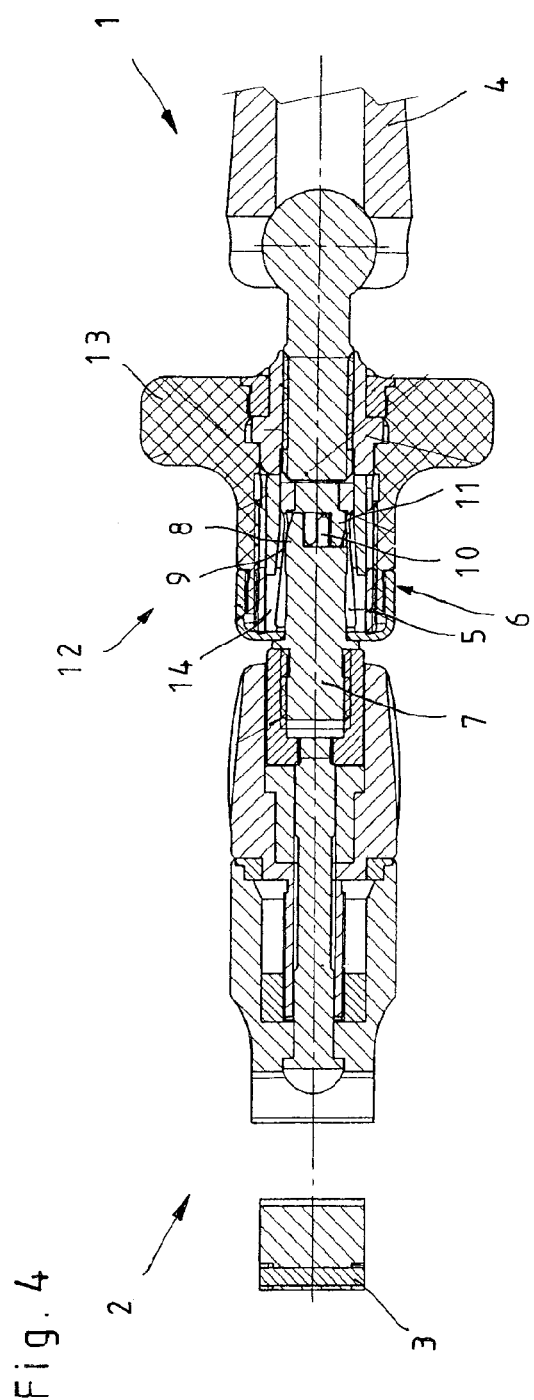

COUPLING DEVICE FOR ATTACHING MEDICAL INSTRUMENTS TO A HOLDING DEVICE

CROSS-REFERENCE TO RELATED APPLICATIONS

The present application claims priority of German patent application No. 10 2007 030 310.8 filed on Jun. 29, 2007, the content of which is incorporated herein by reference.

FIELD OF THE INVENTION

The invention relates to a coupling device for attaching medical instruments to a holding device, having a coupling socket configured on one of the components that are to be connected with one another and a coupling plug that is configured on the other component and can be inserted into the coupling intake. The coupling intake and the coupling plug can be attached with respect to one another in the mutually coupled position by means of at least one blocking element.

BACKGROUND OF THE INVENTION

Coupling devices of this kind are used in the medical field, for instance in endoscopic operations, to secure medical instruments, apparatuses, and/or accessories on holding devices in order to free up the operating physician and/or the physician's assistants. The holding devices thus allow an exactly positioned alignment of the secured instruments. Because it can be necessary during the operation to replace secured medical instruments or the like, it is essential for the coupling systems to be capable of simple and rapid actuation.

A generic coupling device is disclosed, for instance, in DE 203 17 693 U1. With this familiar coupling system, the coupling between the coupler socket and the coupler plug takes place by means of a spring-loaded catch element that is positioned in the coupler socket and that, in coupled position, engages by catching in a circular groove configured in the coupler plug. This familiar construction also permits quick and uncomplicated coupling of the components that are to be joined to one another, but it does not ensure a mounting of the two components to one another that is secure against rotation. In addition, spring-loaded catch elements always have a certain free play in their coupling and are difficult to clean.

Consequently it is the object of the invention to provide a coupling device of the aforementioned type, which allows simplicity of structure while guaranteeing easy, rapid handling.

SUMMARY OF THE INVENTION

This object is achieved according to the invention in that the coupler socket is configured as a sleeve-shaped collet chuck that comprises several spring arms set at distances from one another and the coupler plug comprises a coupling pin that is equipped with at least one catch cam, where the at least one catch cam of the coupling pin in coupled position catches to form a corresponding back-cut on the collet chuck, and in that the locking element can be screwed onto the collet chuck in such a way that the spring arms of the collet chuck are fixed in the coupled position facing outward in the radial direction.

Because of the inventive configuration of the coupler socket and coupler plug as collet chuck and coupling pin that can catch in the collet chuck, a particularly easily and quickly operating coupling connection is provided for the components that are to be connected with one another, namely the medical instrument on the one hand and the holding device on the other. This catch coupling connection is secured in likewise simple and rapid manner by means of the locking element that can screw onto the collet chuck and that, with the components in the mutually coupled position, prevents radial opening of the collet chuck.

It is proposed with a practical embodiment of the invention that the coupler plug should comprise protrusions, which in coupled position interlock with corresponding protrusions of the collet chuck. These protrusions, in addition to affixing the coupling pin in the axial direction in the collet chuck thanks to the catching, ensure a reciprocal securing of the components against rotation.

In order to facilitate the coupling of the coupling pin and collet chuck and to ensure that the coupling pin and collet chuck engage in one another in the foreseen position, according to the invention the flanks of the protrusions of the coupling pin and collet chuck that in coupled position are in contact with one another are configured as tapering so that, because of the tapering shape, an automatic self-centering of the components occurs with respect to one another.

It is further proposed with the invention that the coupling pin of the coupler plug and the coupler socket, which is configured as a collet chuck, should be form-locked with one another in coupled position in order to ensure an exactly positioned fixing of the components to one another without any free play.

According to a first embodiment of the invention it is proposed that the locking element should be configured as a box nut that is mounted so that it can rotate on the coupler socket.

According to a preferred second embodiment of the invention, it is proposed that the locking element should consist of a nut that can screw onto the collet chuck and of a clamping ring that is in active connection with the nut and can be mounted on the collet chuck in the axial direction.

The clamping effect of the clamping ring, which prevents the opening of the collet chuck, can be reinforced according to the invention in that the inside of the clamping ring that faces the collet chuck and the outer surface area of the collet chuck are configured as cones corresponding to one another. This configuration of the mutually facing surfaces as cone and counter-cone causes a form-locking surface pressure, directed radially inward, on the collet chuck and in this way prevents opening of the collet chuck and thus a release of the coupling pin.

Finally, it is proposed with the invention that the collet chuck and clamping ring should be secured by means of at least one securing element preventing rotation with respect to one another. This at least one securing element guarantees that the clamping ring does not rotate together with the nut around the longitudinal axis of the collet chuck when the nut is screwed onto the collet chuck, but instead the rotary motion of the nut is transformed into a linear motion of the clamping ring in the axial direction of the collet chuck.

Additional characteristics and advantages of the invention can be seen from the appended illustrations, in which an embodiment of an inventive coupling device for securing medical instruments to a holding device is depicted in merely exemplary form, without restricting the invention to this embodiment.

BRIEF DESCRIPTION OF THE DRAWINGS

FIG. 2 shows a side view of the coupling device before coupling the couplet socket and coupler plug.

FIG. 3 shows a side view rotated by 90 degree of the coupling device according to FIG. 2, but showing the coupler socket and coupler plug in coupled position.

FIG. 4 shows a longitudinal view along the line IV-IV according to FIG. 3.

DETAILED DESCRIPTION OF THE INVENTION

Figure 1:
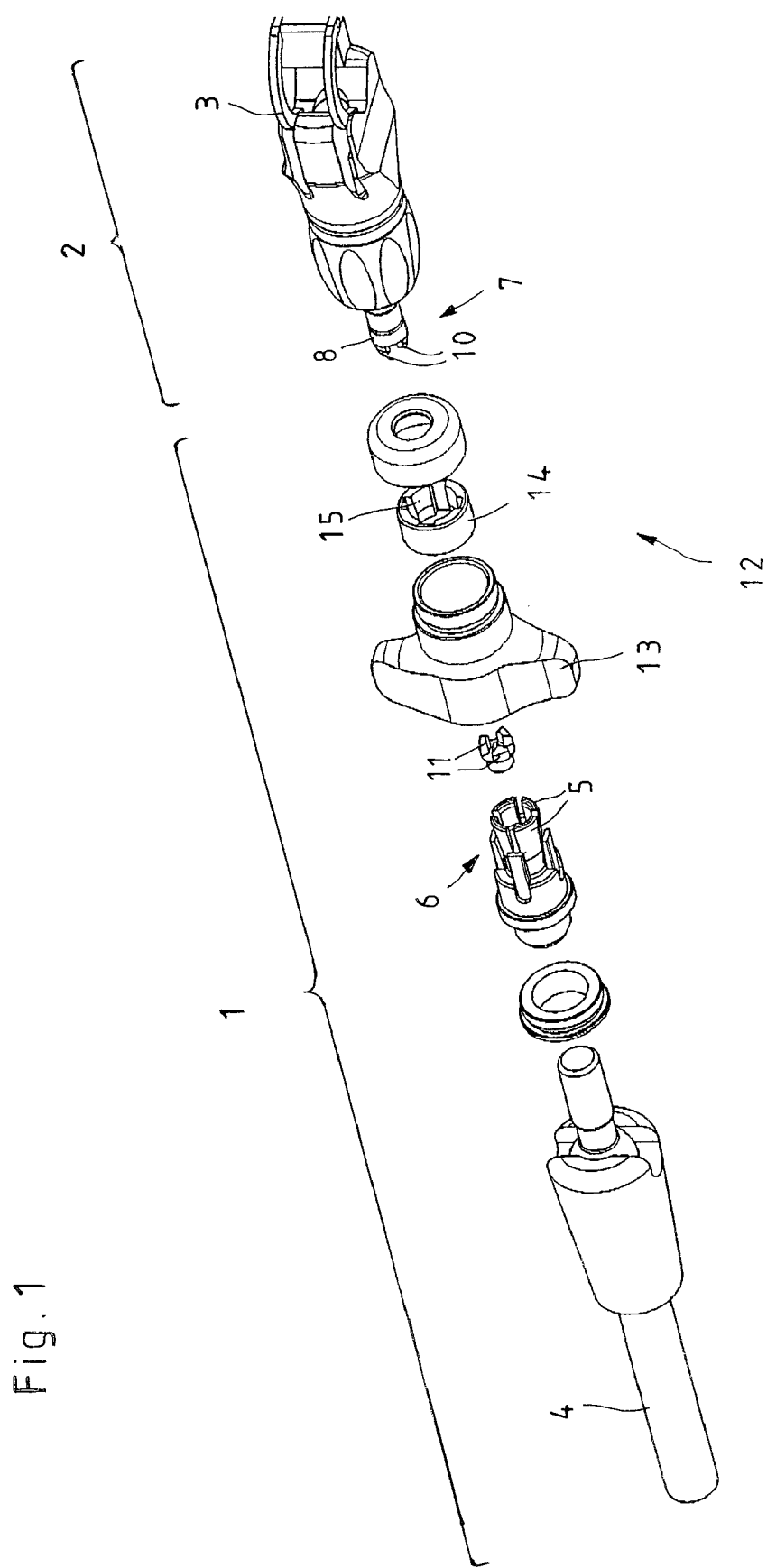
FIG. 1 shows a perspective explosion drawing of an inventive coupling device for securing medical instruments to a holding device.

The coupling device for securing medical instruments onto a holding device depicted in FIGS. 1 through 4 consists essentially of a coupler socket 1 and a coupler plug 2 that can be inserted into the coupler socket 1 to connect the two components that are to be connected to one another, namely a medical instrument 3 on the one hand and a holding device 4 on the other hand, where, as shown in FIGS. 1 through 4, the securing of the medical instrument 3 onto the holding device 4 can occur also indirectly by way of an instrument intake 3 in which the medical instrument 3 in turn can be secured.

Coupling devices of this type are used to be able to secure medical instruments at precise locations on corresponding holding devices to relieve surgical staff during operations.

In the illustrated embodiment the coupler plug 2 is configured on the instrument intake 3 and the coupler socket 1 on the holding device 4. It is also possible of course, without influencing the functioning of the coupling system, to configure the coupler socket 1 on the medical instrument 3 or on the instrument intake 3 and the coupler plug 2 on the holding device 4.

As can be seen in particular from the explosion drawing of FIG. 1, the coupler socket 1 is configured as a sleeve-shaped collet chuck 6 that comprises several spring arms 5 set at intervals from one another. The spring arms 5 surround the intake area in which the coupler plug 2 is found in coupled position. As also shown in FIGS. 1 and 2, the coupler plug 2 is configured as a coupling pin 7 that can be inserted into the collet chuck 6.

In order to secure the coupling pin 7 of the coupler plug 2 and the collet chuck 6 of the coupler socket 1 to one another in the axial direction after they are joined to one another, the coupling pin 7 comprises a catch cam 8 that points radially outward and is configured as a thickening, and which in coupled position engages by catching on a corresponding back-cut 9 on the inside of the spring arms 5. The spring elasticity of the spring arms 5 ensures that the spring arms 5 of the collet chuck 6, because of the catch camp 8, are pressed radially outward and then spring back to catch as soon as the catch cam 8 engages by catching on the back-cut 9 of the spring arms 5.

This catching of the catch cam 8 around the back-cut 9 of the spring arms 5 prevents the combined components—the coupling pin 7 and collet chuck 6—from being able to slip apart again in the axial direction.

In addition, in order to prevent rotation of the components—coupling pin 7 and collet chuck 6—with respect to one another and thus to be able to mount the medical instrument 3 or the instrument intake 3 in exact position in the holding device 4, the coupling pin 7 comprises protrusions 10 that extend in axial direction and, in coupled position, interlock with corresponding protrusions 11 of the collet chuck 6. Thanks to this reciprocal toothed interlocking of the protrusions 10 of the coupling pin 7 and of the protrusions 11 of the collet chuck 6, the two components—coupling pin 7 and collet chuck 6—block one another and thus prevent reciprocal rotation with respect to one another around the longitudinal axis of the coupling device.

Bringing together the coupling pin 7 and the collet chuck 6 is facilitated in the illustrated embodiment in that the flanks of the protrusions 10 and 11 of the coupling pin 7 and collet chuck 6 that are contacting one another in coupled position have a tapered configuration so that, because of the tapering, the components are automatically self-centered.

As further to be seen from FIGS. 1 and 2, the coupling device in addition comprises a locking element 12, by means of which the collet chuck 6 and coupling pin 7 in coupled position can be locked in position with respect to one another in such a way that the locking element 12 prevents any opening of the collet chuck 6 by the spring arms 5 bending apart.

In the illustrated embodiment of the coupling device the locking element 12 consists of a nut 12 that can be screwed onto the collet chuck 6 and a clamping ring 14 that is in active connection with the nut 13 and can be slid onto the collet chuck 6 in axial direction. To prevent the clamping ring 14 from turning with the nut 13 when the nut 13 is screwed on, the collet chuck 6 and clamping ring 14 are secured against rotation with respect to one another by means of at least one securing element 15, for instance protrusions and corresponding recesses. In the illustrated embodiment the nut 13 is configured as a turning handle, by means of which the actuation of the locking element 12 is clearly facilitated.

Connecting the coupler socket 1 with the coupler plug 2 of a coupling device in accordance with FIGS. 1 and 2 occurs as follows:

To secure the medical instrument 3 or instrument intake 3 on the holding device 4, the coupling pin 7 of the coupler plug 2 configured in this embodiment on the instrument intake 3 is inserted into the coupler socket 1 of the holding device 4 which is configured as a collet chuck 6.

Thanks to the catch cams 8 formed on the front area of the coupling pin 7, the spring-elastic spring arms 5 of the collet chuck 6, upon insertion of the coupling pin 7 into the collet chuck 6, are bent radially outward until the catch cam 8 engages by catching on the back-cut 9 configured on the inside of the collet chuck 6. As soon as the coupling pin 7 has been inserted that far into the collet chuck 6, the catch arms 5 spring back into their original position and thus stop the coupling pin 7 in axial direction so that it cannot be dislocated out of the collet chuck 6.

In addition to the catch cam 8 catching with the back-cuts 9, the tapering shapes of the protrusions 10 formed on the coupling pin 7 come into contact with the corresponding protrusions 11 of the collet chuck 6 and position the coupling pin 7 and the collet chuck 6 so that they center themselves and cannot rotate with respect to one another.

To prevent the spring arms 5 of the collet chuck 6 from being able to be bent radially outward, for example by means of a strong axial pulling motion contrary to the insertion direction of the coupling pin 7, and thus from breaking the catching connection between the coupling pin 7 and the collet chuck 6, the locking element 12 is actuated after insertion of the coupling pin 7 and catching with the collet chuck 6 in order to brace the spring arms 5 of the collet chuck 6 in coupled position against any motion directed radially outward.

For this purpose the nut 13 that is in active connection with the clamping ring 14 is screwed onto the collet chuck 6, and the rotation of the nut 13 causes a displacement of the clamping ring 14 in axial direction onto the collet chuck 6.

The clamping effect of the clamping ring 14, which prevents opening of the collet chuck 6, is reinforced in the illustrated embodiment in that the inside of the clamping ring 14 facing the collet chuck 6 and the outer enclosing surface of the collet chuck 6 are configured as cones corresponding to one another. This configuration of the facing surfaces as cone and counter-cone causes a form-locking surface pressure directed radially inward onto the collet chuck 6 and thus prevents opening of the collet chuck 6 and thereby the release of the coupling pin 7.

Release of the coupling occurs in the reverse sequence, starting with the release of the locking element 12. Upon unscrewing the nut 13 from the collet chuck 6, the clamping ring 14 is pushed downward from the collet chuck 6 by the nut 13 and thus releases the spring arms 5 of the collet chuck 6 again. Then, as soon as an axially working pulling force is exerted by means of the coupling pin 7, the catch cam 8 of the coupling pin 7 presses the spring arms 5 of the collet chuck 6 radially outward again until the catch cam 8 goes out of engagement with the back-cut 9 of the collet chuck 6 and the coupling pin 7 subsequently can be pulled out of the collet chuck 6 again.

A coupling device of this configuration is distinguished in that it combines simplicity of structure with an exact positioning of the medical instrument 3 or the instrument intake 3 and in addition ensures simple and rapid handling.

What is claimed is:

1. A coupling device for securing medical instruments to a holding device, having a coupler socket configured on one of the components that are to be coupled to one another and a coupler plug configured on the other component and insertable in the coupler socket, where the coupler socket and the coupler plug can be affixed with respect to one another in the position coupled to one another by means of at least one locking element, wherein the coupler socket is configured as a sleeve-shaped collet chuck comprising several spring arms set apart from one another and the coupler plug comprises a coupling pin equipped with at least one stopping cam pointing outward, where the at least one stopping cam of the coupling pin in coupled position catches to form a corresponding back-cut on the collet chuck and the locking element can be screwed onto the collet chuck in such a way that the spring arms of the collet chuck are affixed in the coupled position facing outward in the radial direction and wherein the coupling pin comprises several protrusions set apart from one another that extend in the axial direction and which in the coupled position mesh with corresponding protrusions of the collet chuck.

2. The coupling device according to claim 1, wherein the flanks of the protrusions of the coupling pin and of the collet chuck that are in contact with one another in coupled position have a tapered configuration.

3. The coupling device according to claim 1, wherein the coupling pin of the coupler plug and the coupler socket configured as a collet chuck are, in coupled position, in a form-locking connection to one another.

4. The coupling device according to claim 1, wherein the locking element is configured as a box nut mounted so that it can rotate on the coupler socket.

5. The coupling device according to claim 1, wherein the locking element consists of a nut that can be screwed onto the collet chuck and of a clamping ring that is in active connection with the nut and can be inserted in axial direction onto the collet chuck.

6. The coupling device according to claim 5, wherein the inside of the clamping ring facing the collet chuck and the outer enclosing surface of the collet chuck are configured as mutually corresponding cones.

7. The coupling device according to claim 6, wherein the collet chuck and clamping ring are secured by at least one securing element so that they cannot rotate relative to one another.

8. The coupling device according to claim 5, wherein the collet chuck and clamping ring are secured by at least one securing element so that they cannot rotate relative to one another.

* * * * *